United States Patent [19]
Chiou

[11] Patent Number: 5,240,936
[45] Date of Patent: Aug. 31, 1993

[54] TREATING OR PREVENTING OCULAR INFLAMMATION OR SYSTEMIC IMFLAMMATORY DISEASE

[75] Inventor: George C. Y. Chiou, College Station, Tex.

[73] Assignee: Texas A&M University System, College Station, Tex.

[21] Appl. No.: 883,028

[22] Filed: May 14, 1992

[51] Int. Cl.$^5$ ............................................ A61K 31/44
[52] U.S. Cl. ..................................... 514/297; 514/912
[58] Field of Search ........................ 514/297, 309, 912

[56] References Cited

PUBLICATIONS

Remington's Pharmaceutical Sciences. Fifteenth Edition 1975. pp. 1491-1492.
Ellis, *Ocular Therapeutics and Pharmacology*, C. B. Mosby Co., (1985) pp. 212-227.
Polansky et al., "Anti-Inflammatory Agents, Steroids as Anti-Inflammatory Agents" in Sears, ed., *Handbook of Experimental Pharmacology*, Springer-Verlag, (1985), 69: 459-538.
Miyano et al., [Ophthalmic Research, (1984), 16: 256-263.
Chiou et al., *Journal of Ocular Pharmacology*, (1985), 1: 383-390.
Bhattacherjee et al., "Effect of Lipoxygenase Products on Leukocyte Accumulation in the Rabbit Eye" in Samuelsson et al., Eds., *Leukotrienes and Other Lipoxygenase Products*, Raven Press, (1982), 325-330.
Chang et al., *Journal of Ocular Pharmacology*, (1989), 5: 353-360.

*Primary Examiner*—Zohreh A. Fay
*Attorney, Agent, or Firm*—Morrison & Foerster

[57] ABSTRACT

A novel compound for controlling (treatment and prevention) of ocular inflammation or systemic inflammatory disease is disclosed. The compound, OB-186, is effective at both the early and late phases of inflammation. The compound is useful for the treatment or prevention of inflammation in both the anterior and posterior portions of the eye and systemic inflammatory diseases, such as rheumatoid arthritis, inflammatory bowel disease, glyomerulonephritis, allergic inflammation and allergic encephalomyelitis.

12 Claims, 6 Drawing Sheets

TREATING OR PREVENTING OCULAR INFLAMMATION OR SYSTEMIC IMFLAMMATORY DISEASE

TECHNICAL FIELD

The present invention relates generally to controlling (treatment and/or prevention) of ocular inflammation or systemic inflammatory disease. More specifically it relates to a novel compound shown to be an effective ocular antiinflammatory agent and in systemic administration against inflammation.

BACKGROUND OF THE INVENTION

Ocular inflammation may occur in many different areas of the eye. One type of ocular inflammation, uveitis, is the inflammation of the uveal tract. Endogenous uveitis is caused by various systemic processes or intraocular disorders whereas exogenous uveitis is the result of the accidental introduction of pathogenic organisms or foreign substances into the eye. Endogenous uveitis may be classified in many ways, including anterior, posterior and diffuse. The most commonly occurring types of uveitis, such as histoplasmosis, toxoplasmosis and toxocariasis, affect the posterior part of the eyes which are difficult, if not impossible, for locally instilled eye drugs to reach. Peripheral uveitis, ankylosing spondylitis, herpes simplex, herpes zoster, tuberculosis and endophthalmitis phacoanaphylactica occur in the anterior part of the eyes. Toxoplasmosis, peripheral uveitis, syphilis, tuberculosis, sarcoidosis and Vogt-Koyanagi-Harada syndrome may occur in both the anterior and posterior segments of the eye. Although the etiology of these diseases can be different, they have the common manifestation of ocular inflammation.

Uveitis has been treated with corticosteroids, non-steroidal anti-inflammatory agents, immunosuppressives and a combination of cycloplegics and mydriatics. However, treatment of uveitis with drugs used to treat systemic disorders is not always effective. (Ellis, *Ocular Therapeutics and Pharmacology*, C. B. Mosby Co., (1985) pp. 212-227.) Furthermore, very high doses of corticosteroids (100 mg daily) must be used in severe and acute posterior uveitis. Such doses can cause severe complications. Thus, the amounts administered should be reduced when clinical improvement occurs. However, reduction below 15-20 mg/day can result in reoccurrences of the disease.

Since uveitis is considered to be an autoimmune disease, treatment with immunosuppressive agents, such as alkylating agents and antimetabolites, including the drug cyclosporine, is being studied. However, the use of these agents may produce many serious side effects, including bone marrow depression, thrombocytopenia, leukopenia, bleeding, nausea, vomiting and stomatitis. The use of these substances in the treatment of uveitis is still investigational.

In order to avoid serious side effects in the treatment of uveitis, non-steroidal anti-inflammatory agents (NSAIAs) such as salicylates, phenylbutazone, indomethacin, ibuprofen and naproxen have been tried. The results have not been satisfactory. Furthermore, these NSAIAs also can produce numerous side effects, including edema, nausea, stomatitis, epigastric pain, peptic ulcer, agranulocytosis, hepatitis and drug rash.

Ocular inflammation may additionally occur in the anterior portion of the eye following ocular surgery. Steroidal and nonsteroidal antiinflammatory agents have been used to relieve the inflammation. However, steroidal agents can induce an increase in intraocular pressure (Polansky et al., "Antiinflammatory Agents", in Sears, ed., *Handbook of Experimental Pharmacology*, Springer-Verlag, (1985), 69:459-538). NSAIAs may actually worsen the inflammation, especially during the late phase of the inflammation. This is because the clinically available NSAIAs at this time are primary cycloxygenase inhibitors. Blocking the cycloxygenase arm of the arachidonic acid (AA) cascade potentiates the production of lipooxygenase metabolites which are ultimately the leukotrienes (LT). LTs are responsible for the late phase of inflammation and for the chemotaxis of leukocytes (Miyano et al., *Ophthalmic Res.* (1984) 16:256-263; Chiou et al., *J. Ocular Pharmacology* (1985) 1:383-389; Bhattercherjee et al., "Effects of lipooxygenase products on leukocyte accumulation in the rabbit eye" in Samuelsson et al., eds., *Leukotrienes and Other Lipooxygenase Products*, Raven Press (1982) 325-330.) A previous study indicated that a new synthetic lipooxygenase inhibitor, REV 5901, was effective in reducing the late phase of inflammation. However, when REV 5901 was used alone in treatment of lens protein induced ocular inflammation, there was an increase in the early phase of inflammation. This observation was attributed to an increase in the production of prostaglandins caused by the inhibition of the lipooxygenase arm of the AA cascade. (Chang et al., *J. Ocular Pharmacology*. (1989) 5:353-360). The early phase of the inflammation has been effectively suppressed by indomethacin.

DISCLOSURE OF THE INVENTION

The present invention relates to a method for controlling (prevention and/or treatment) of ocular inflammation or systemic inflammatory disease. In one embodiment, the invention is drawn to the use of a new agent, OB-186, as an ocular antiinflammatory agent. The formula of this compound is as follows:

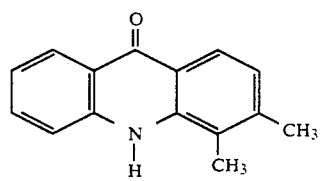

In a second embodiment, the invention involves a pharmaceutical preparation for use in the controlling (prevention and/or treatment) of ocular inflammation or systemic inflammatory disease which comprises the above compound in admixture with a pharmaceutically acceptable excipient.

DETAILED DESCRIPTION OF THE INVENTION

Figure 1:
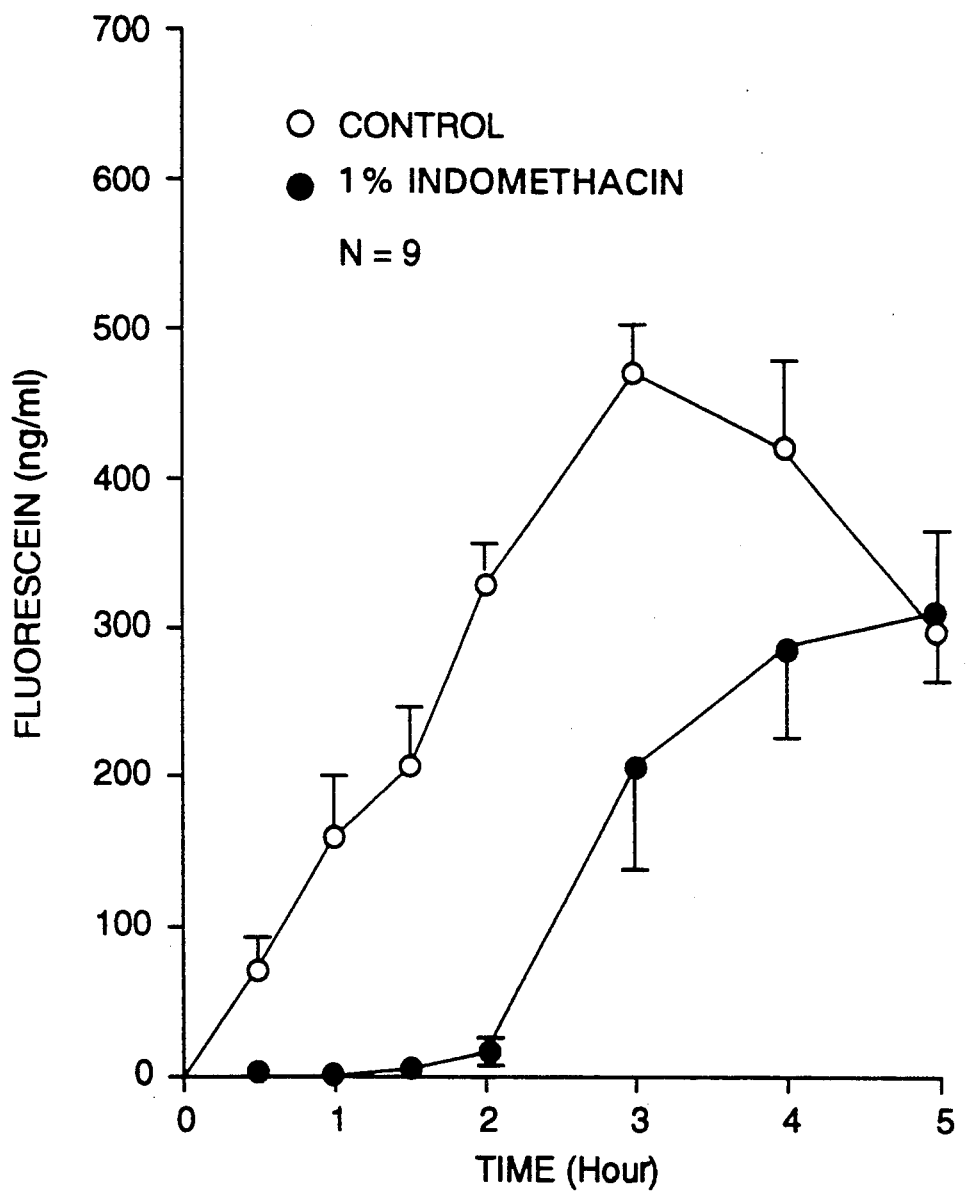
FIG. 1 shows a comparison of the effects of 1% indomethacin on ocular inflammation induced by lens protein injected intracamerally to that of a control that received no drug. Each point is a mean of 9 values for fluorescein concentration in the anterior chamber of the eye. The bars represent the standard error of the mean ("SEM").

The present invention is applicable to ocular inflammation at both the early and late phases of inflammation. OB-186 has been tested for suppression of ocular inflammation and found to reduce inflammation induced in the iris, the ciliary body and the retina. Further tests indicate that OB-186 is also useful for the treatment of posterior uveitis. Additionally, unlike the non-steroidal antiinflammatory agents (NSAIAs), OB-186 does not produce the numerous side effects associated with corticosteroids. Since endotoxin--induced posterior uveitis is inhibited by OB-186 via systemic administration, OB-186 also can inhibit systemic inflammation diseases including rheumatoid, inflammatory bowel disease, glomerulonephritis, allergic inflammation, allergic encephaliomyelitis, and the like.

DEFINITIONS

In this specification and in the claims which follow, reference will be made to a number of terms which shall be defined to have the following meanings:

"Controlling" as used herein refers to treatment and/or prevention.

"Treatment" as used herein refers to the reduction or elimination of inflammation (therapy).

"Prevention" refers to the treatment of surgical patients to avoid inflammation (prophylaxis).

"Inflammation-controlling effective amount" refers to the amount of the pharmaceutically active substance sufficient to elicit at least a desired threshold response to the substance in a subject to which the substance is administered, whether therapeutic or prophylactic.

"Pharmaceutically active substance" as used herein refers to a substance that has been shown to be useful in controlling (treatment and/or prevention) of ocular inflammation and/or systemic inflammatory disease. In the present invention, pharmaceutically active substances include OB-186, indomethacin, REV 5901, and prednisolone.

"Pharmaceutical composition" refers to a composition containing the pharmaceutically active substance. The composition may also contain a pharmaceutically acceptable vehicle.

Process for Preparation

OB-186 may be prepared according to the methods described in Example 1 below.

Administration

The administration of OB-186 described herein can be via any of the accepted modes of administration of pharmaceutical compositions. These methods for treating and preventing ocular inflammation, of systemic processes or intraocular disorders, include topical administration of solutions, suspension ointments or gels, parenteral injection, or oral administration. Systemic administration in treating or preventing inflammation is very applicable with OB-186.

Depending on the intended mode of administration, the compositions may be in the form of solid, semi-solid or liquid dosage forms, such as for example, tablets, pills, capsules, powders, liquids, suspensions, or the like, preferably in unit dosage forms suitable for single administration of precise dosages. The compositions will include a conventional pharmaceutical vehicle and, in addition, may include other medicinal agents, pharmaceutical agents, carriers, adjuvants, diluents, etc. The amount of active compound administered will, of course be dependent on the subject being treated, the manner of administration and the judgment of the prescribing physician.

The conventional pharmaceutical vehicle should be compatible with the pharmaceutically active substance of the pharmaceutical composition. Suitable vehicles for ocular use are, for example, sterile isotonic solutions such as isotonic sodium chloride or boric acid solutions. These vehicles typically contain sodium chloride or boric acid, respectively, as well as benzalkonium chloride and sterile distilled or purified water. Also useful is phosphate buffered saline (PBS), pH 7.4. Other suitable vehicular constituents include phenylmercuric nitrate, sodium sulfate, sodium sulfite, disodium phosphate and monosodium phosphate.

The compositions may also contain auxiliary substances i.e. antimicrobial agents such as chlorobutanol, parabans or organic mercurial compounds; pH adjusting agents such as sodium hydroxide, hydrochloric acid or sulfuric acid; and viscosity increasing agents such as methylcellulose. One of ordinary skill in the art will easily find substitutions for the above auxiliary substances. The final composition should be sterile, essentially free of foreign particles, and have a pH that allows for optimum drug stability. Generally pH values in the range of 5-8 will find use with the subject composition. Preferably, the pH will be as close to the pH of tear fluid, i.e. 7.4, as possible.

Typically the compositions of the subject invention are prepared as solutions, suspensions, ointments, gels, or ocular delivery devices such as drug-impregnated solid carriers that are inserted into the eye. If such a carrier is used, the above-mentioned vehicles are unnecessary. A variety of polymers can be used to formulate ophthalmic drug carriers. Saettone, M. F., et al., *J. Pharm. Pharmocol.* (1984) 36:229, and Park, K. et al., in *Recent Advances in Drug Delivery Systems,* Anderson et al, eds., Plenum Press (1984) 163–183, describe such polymers, the disclosures of which are incorporated herein by reference in their entirety. Drug release is generally effected via dissolution or bioerosion of the polymer, osmosis, or combinations thereof. The device should be formulated to release the drug at a rate that does not significantly disrupt the tonicity of tear fluid.

More specifically, several matrix-type delivery systems can be used with the subject invention. These systems are described in detail in Ueno et al., "Ocular Pharmacology of Drug Release Devices", in *Controlled Drug Delivery,* Bruck, ed., vol. II, Chap 4, CRC Press Inc. (1983), the disclosure of which is incorporated herein by reference in its entirety. Such systems include hydrophilic soft contact lenses impregnated or soaked with the desired drug, as well as biodegradable or soluble devices that need not be removed after placement in the eye. These soluble ocular inserts can be composed of any degradable substance that can be tolerated by the eye and that is compatible with the drug to be administered. Such substances include but are not limited to poly(vinyl alcohol), polymers and copolymers of polyacrylamide, ethylacrylate, and vinylpyrrolidone, as well as cross-linked polypeptides or polysaccharides, such as chitin.

Capsule-type delivery systems will also find use with the instant invention. These systems, described in Ueno et al., supra, utilize polymer membranes to control the release of the drug in question. These devices are particularly useful for the delivery of hydrophilic drugs. Hydrophobic drugs can be administered via a silicone rubber device such as described in Ueno et al., supra.

(Ophthalmic) ointments will include a base, generally composed of white petrolatum and mineral oil, often with anhydrous lanolin. Polyethylene-mineral oil gel is also satisfactory, as are other substances that are non-irritating to the eye, permit diffusion of the drug into the ocular fluid, and retain activity of the medicament for a reasonable period of time under storage conditions. If suspensions are used, the particle sizes therein should be less that 10 $\mu$m to minimize eye irritation. Furthermore, if solutions or suspensions are used, the amount delivered to the patient should not exceed 50 $\mu$l, preferably 25 $\mu$l or less, to avoid excessive spillage from the eye.

For solid compositions, conventional nontoxic solids including, for example, pharmaceutical grades of mannitol, lactose, starch, magnesium stearate, sodium saccharin, talc, cellulose, glucose, sucrose, magnesium carbonate, and the like may be used. Liquid pharmaceutically administrable compositions can, for example be prepared by dissolving, dispersing, etc. an active compound as defined above and optional pharmaceutical adjuvants in a vehicle, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Company, Easton, Pennsylvania, 15th Edition, 1975.

For oral administration, i.e., of any of the present compounds which may be orally active, a pharmaceutically acceptable nontoxic composition is formed by the incorporation of any of the normally employed vehicles described above. Such compositions take the form of solutions, suspensions, tablets, pills, capsules, powders, sustained-release formulations and the like. Such compositions may contain 1%–95% active ingredient, preferably 1–10%. An inflammation-controlling effective amount for purposes of preventing or treating ocular inflammation is usually in the range of 1–50 mg/kg. In order to prevent inflammation in surgical patients, the compound should be administered prior to surgery. For example, the compound may be administered 2–15 hours prior to surgery. Preferably, the compound is administered in multiple doses every 2–6 hours for 10–15 hours prior to surgery. For best results, the compound is administered 12, 8, and 2 hours prior to surgery. Similarly, the compound should, for best results, be administered following surgery in multiple doses. For example, the compound can be administered for 3–10 days post surgery every 4–8 hours. Preferably, the compound is administered every 6 hours following surgery for 5–7 days. In order to treat inflammation, the compound should be administered every 4–8 hours for 3–10 days. Preferably, the compound is administered every 6 hours for 5–7 days.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable vehicles are, for example, water, saline, dextrose, glycerol, ethanol or the like. In addition, if desired, the pharmaceutical compositions to be administered may also contain minor amounts of nontoxic auxiliary substances such as wetting or emulsifying agents, pH buffering agents and the like, such as, for example, sodium acetate, sorbitan monolaurate, triethanolamine oleate, etc. An inflammation-controlling effective amount for purposes of preventing or treating ocular inflammation is usually in the range of 0.1–20 mg/kg. The compound is administered as described above with regard to oral administration.

The subject compounds can also be administered by implantation of a slow-release or sustained-release system, such that a constant level of dosage is maintained. For a review of these sustained release systems see Ueno, et al., "Ocular Pharmacology of Drug Release Devices", in *Controlled Drug Delivery,* Bruck, ed., vol. II, Chap 4, CRC Press Inc. (1983). An inflammation-controlling effective amount for purposes of preventing or treating ocular inflammation is usually in the range of 0.1–20 mg/kg/day. The system can be implanted after surgery in order to prevent inflammation. In order to treat inflammation, a new implant is inserted every 3–10 days for up to 60 days. Preferably, a new implant is inserted every 5–7 days for up to 30 days.

Topical administration of OB-186 in the form of eyedrops was found to be effective in inhibiting anterior ocular inflammation induced by lens protein injected into the anterior chamber. These results indicate that OB-186 can cross the cornea barrier effectively to inhibit the inflammation inside the eyeball. OB-186 also can cross the blood eye barrier and inhibit uveitis after systemic administration. The results obtained in this study supported this as well. An inflammation-controlling effective amount for purposes of preventing or treating ocular inflammation is usually in the range of 0.1–20 mg/kg. The compound is administered as described above with respect to oral administration.

Eyedrops are most effective for inflammation of the anterior portion of the eye. For posterior uveitis, injection or oral administration is preferred.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLES

Example 1

Synthesis of OB-186-3,4-dimethyl-9(10H)-acridone

A suspension of mefenamic acid (0.24 g, 1 mmol) in polyphosphoric acid (1.0 g) was heated at 130° C. for one hour. A yellowish viscous mixture was cooled. Water (10 ml) was gradually added to separate solid, which was collected and washed with water and recrystallized from EtOH to give the desired product as yellowish crystals, mp>300° C., yield 0.14 g (62.8%). IR$\nu^{KBr}$: 3250(NH), 1625(C=O)$^{cm-1}$. m/z (M+):223. Anal. Calcd. for $C_{15}H_{13}NO$ C,80.69; H, 5.87; N, 6.27. Found: C, 80.35; H, 5.78; N, 6.10.

Example 2

Effects of Various Compositions on Lens Protein Induced Inflammation

A. Materials

Indomethacin was purchased from Sigma (St. Louis, Mo.). REV 5901 was obtained from Revlon Health Care Group (Tuckahoe, N.Y.). A 1% ophthalmic solution of prednisolone (1% Econopred) was purchased from Alcon (Fort Worth, Texas). OB-186 was obtained from Dr. T. Okawara at the University of Kumamoto. Indomethacin, REV 5901 and OB-186 were dissolved in polyethylene glycol (molecular weight 200) (60%) and then diluted with aqueous solution (40%) to a final concentration of 1%.

Fluorescein-labeled dextran with molecular weight of 70,000 (FD 70) was obtained from Sigma. 100 mg of FD 70 was initially dissolved in phosphate buffer saline (Sigma) and passed through a PD 10 column (Pharmacia). This solution was then diluted with heparinized normal saline to make a final concentration of a vehicle of 10 mg/ml FD 70 and 100 U/ml of heparin.

Lens protein was prepared and protein concentration was determined according to procedures described in Miyano et al. *Ophthalmic Res.* (1984) 16:256–263. The quantity of lens protein in the lens protein preparation was 29.67 mg/ml.

B. Methods

New Zealand White albino rabbits of either sex weighing 2.0 to 3.0 kg were used. The rabbits were initially anesthetized with 25 mg/kg of ketamine and 5 mg/kg of xylazine given intramuscularly. Half of the above dosage was given hourly for the remainder of the experiment. 15 minutes after the anesthesia, 50 µl of the solvent was instilled into the right eye. 50 µl of drug solution was instilled into the left eye. One hour after the application of the drug and the vehicle, 24 µl of the lens protein was injected into the anterior chamber with a 30 gauge needle. Extreme care was taken to avoid traumatizing the iris. Fifteen minutes after the injection of the lens protein, FD 70 (1.4 mg/kg) was injected via a marginal ear vein. The rabbits were euthanized at the end of the experiment with an injection of 10 ml of air through the marginal ear vein.

Scanning of the eyes was done by the use of a fluorophotometer (Fluorotron Master, Coherent Corp., Palo Alto, Calif.). Measurements were done at 0, 30, 60, 90, 120, 180, 240, and 300 minute intervals. The measurements are reported in FIGS. 1–4 and are expressed in ng/ml of FD 70 in the anterior chamber.

C. Results

All data were analyzed with Student's t-test for two values and analysis of variance for more than two values. Each value was expressed as mean ± standard error of the mean. A p value of 0.05 or less was considered significant.

FIGS. 1–4 describe the effects of the various compounds on lens protein induced inflammation. The greater the permeability of fluorescein from the blood stream into the eye, the greater the degree of inflammation.

Figure 2:
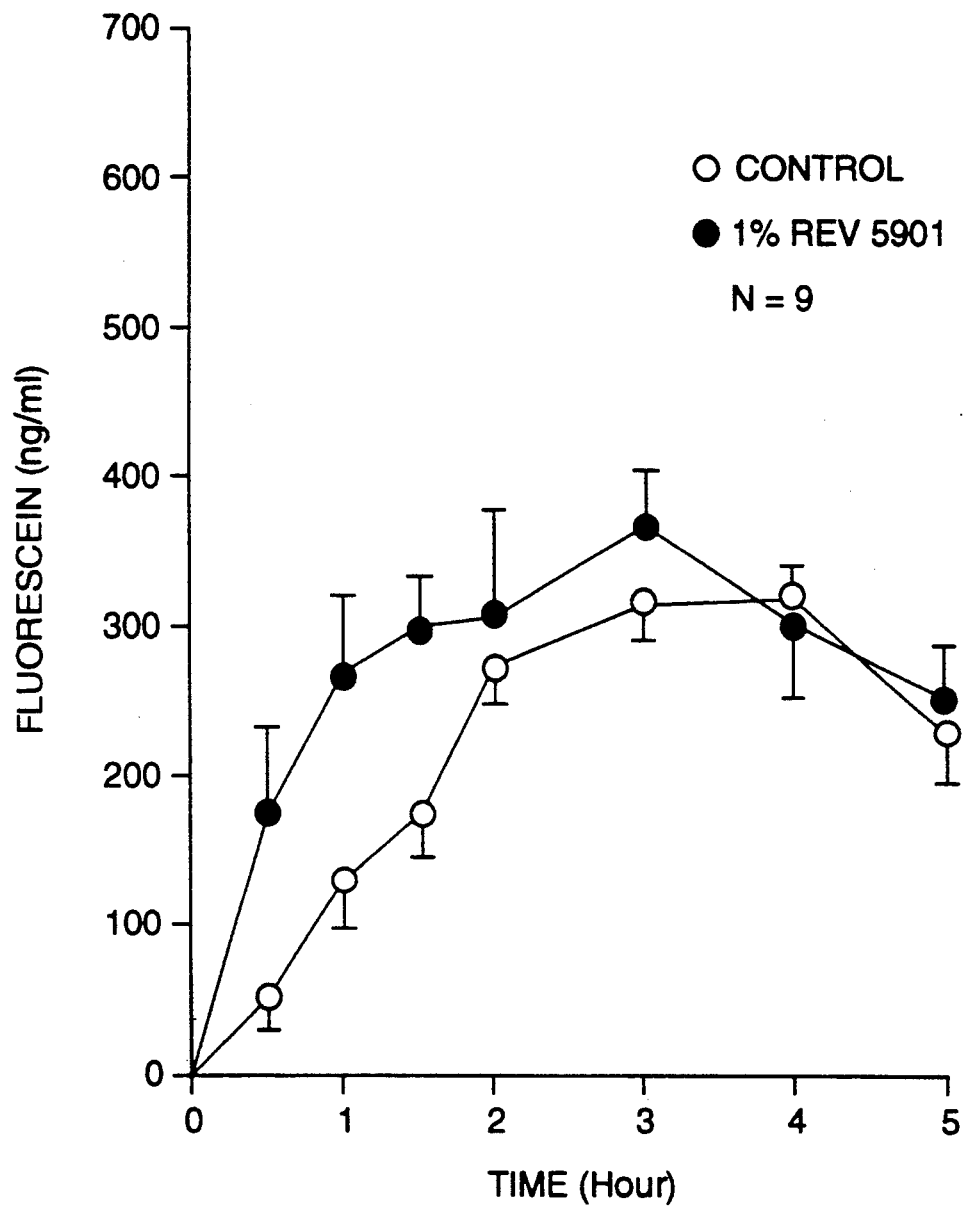
FIG. 2 depicts the effects of 1% REV 5901 on ocular inflammation induced by lens protein injected intracamerally as opposed to that of a control without the drug. Each point is a mean of 9 values for fluorescein concentration in the anterior chamber of the eye. The bars represent the SEM.
Figure 3:
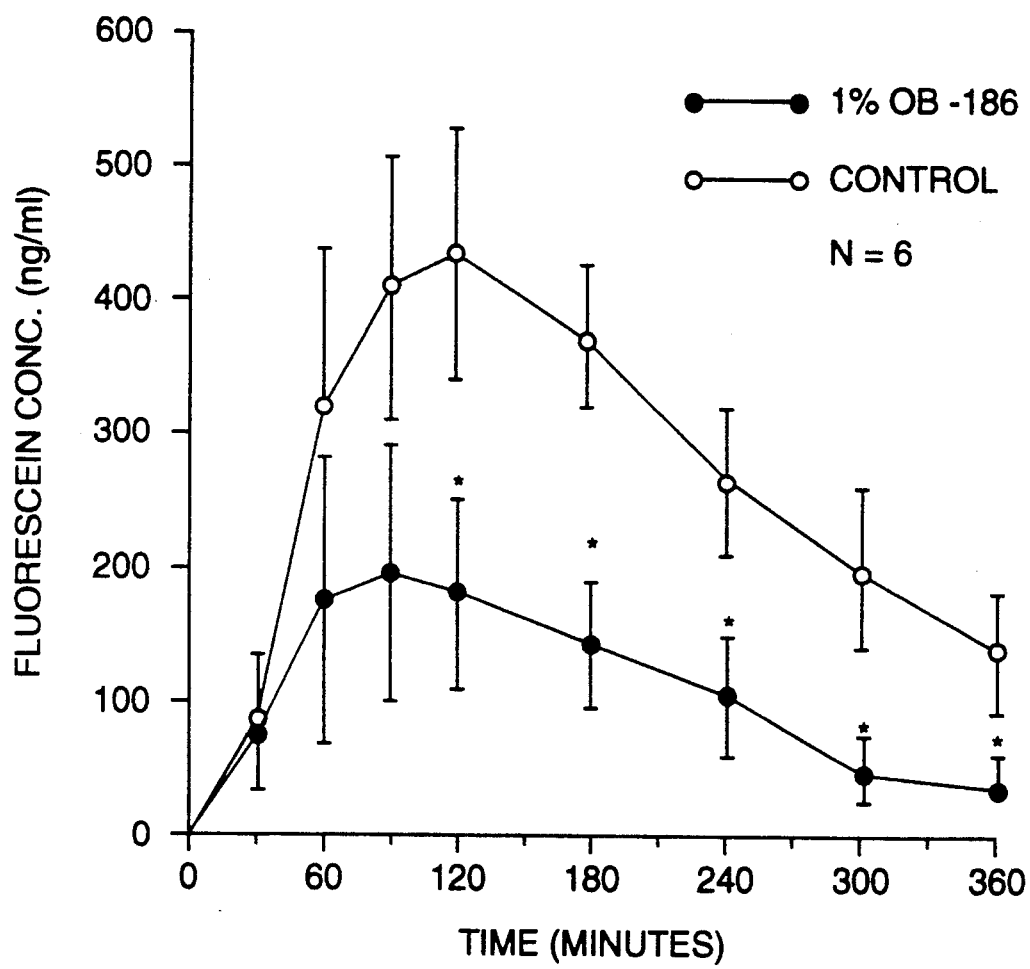
FIG. 3 shows a comparison of the effects of 1% OB-186 on ocular inflammation induced by lens protein injected intracamerally to that of a control that received no drug. Each point is a mean of 6 values for fluorescein concentration in the anterior chamber of the eye. The bars represent the SEM, and the asterisks indicate the significant difference from the corresponding control values at $p<0.05$.
Figure 4:
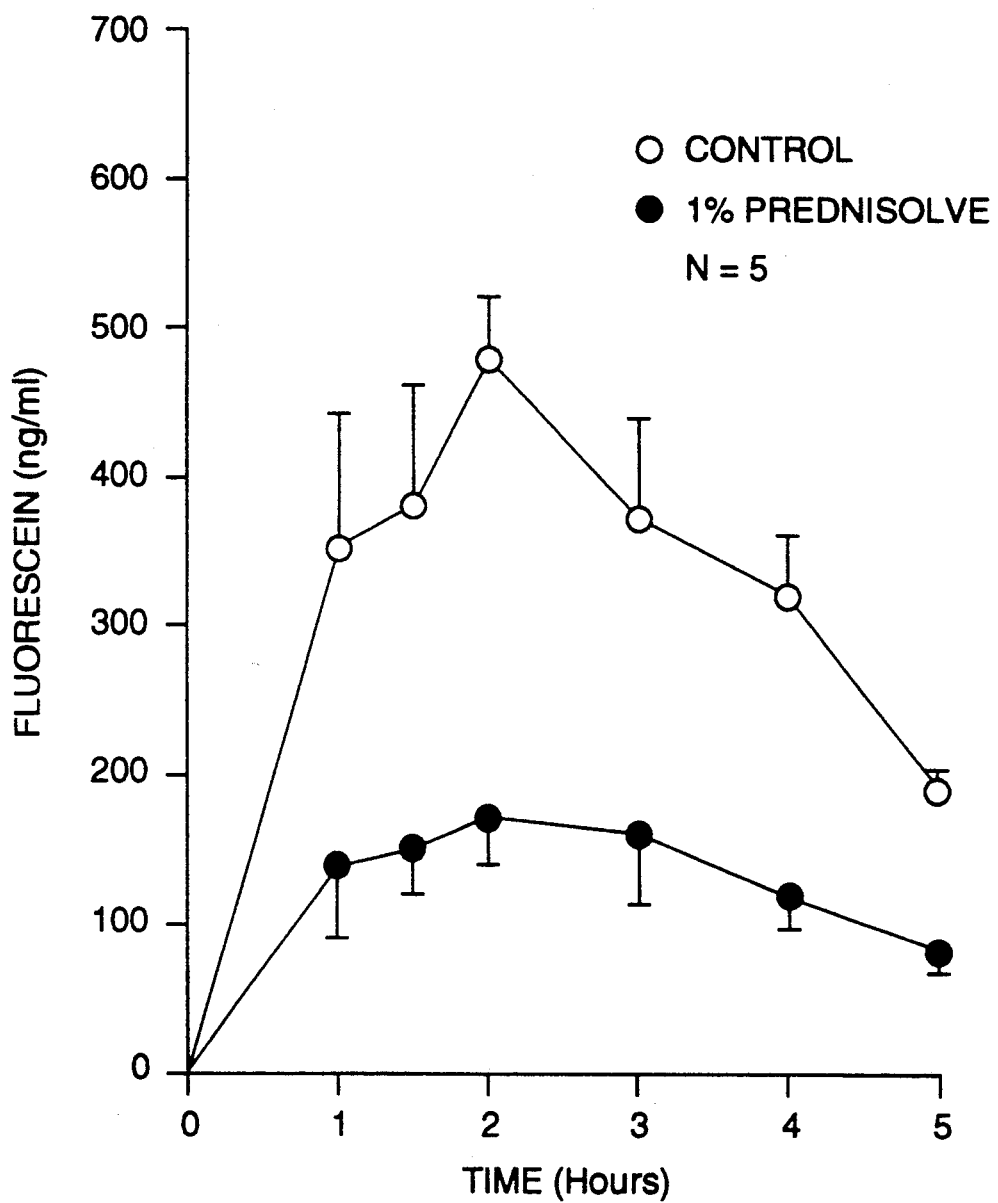
FIG. 4 depicts the effects of 1% prednisolone on ocular inflammation induced by lens protein injected intracamerally as opposed to that of a control without the drug. Each point is a mean of 5 values for fluorescein concentration in the anterior chamber of the eye. The bars represent the SEM.

The early phase of this lens protein induced inflammation (0–3 hours) was effectively suppressed by indomethacin but not the late phase (4–5 hours) (FIG. 1). On the other hand, REV 5901 reduced the late phase of inflammation but worsened the early phase (FIG. 2). OB-186 suppressed ocular inflammation (FIG. 3) about as effectively as did prednisolone (FIG. 4) at both the early and late phases of inflammation.

Example 3

Effects of OB-186 on Endotoxin-Induced Posterior Uveitis

A. Materials

OB-186 was synthesized with the method of Example 1 above. Since OB-186 is not soluble in the aqueous medium, a suspension was prepared using a combined vehicle of Tween 80 (6%), PEG 400 (20%) and DMSO (20%), and the remainder distilled water.

Fluorescein labelled dextran with a molecular weight of 70,000 (FD 70) was obtained from Sigma and was prepared into a solution as described previously in the section on Fluorophotometric Methods in rabbit experiments with lens protein-induced inflammation (Example 2).

B. Methods

Sprague-Dawley rats weighing 250–350 grams were anesthetized with 35 mg/kg ketamine and 5 mg/kg xylazine intramuscularly. 10 µl of 10 ng endotoxin was injected intravitreally, and the animals were allowed to recover from the anesthesia. OB-186 at doses of 10 mg/kg and prednisolone at a dose of 10 mg/kg were injected intraperitoneally at times 0, 4, and 10 hours after the endotoxin injection. The uveitis was measured with a Fluorotron (fluorophotometer) at 12 hours after the endotoxin injection. The procedure of Fluorotron measurement was the same as described previously in rabbit experiments with lens protein induced inflammation (Example 2). At the end of the experiments, the rats were euthanized with 100 mg/kg of pentobarbital sodium.

All data were analyzed with Student's t-test for two values and analysis of variance for more than two values. Each value was expressed as mean ± standard error of the mean. A p value of 0.05 or less was considered significant.

C. Results

When fluorescein solution was injected intravenously into rats 12 hours after the endotoxin injection, the fluorescein reached peak in the eyes at 6-8 hours after the fluorescein injection.

Figure 5:
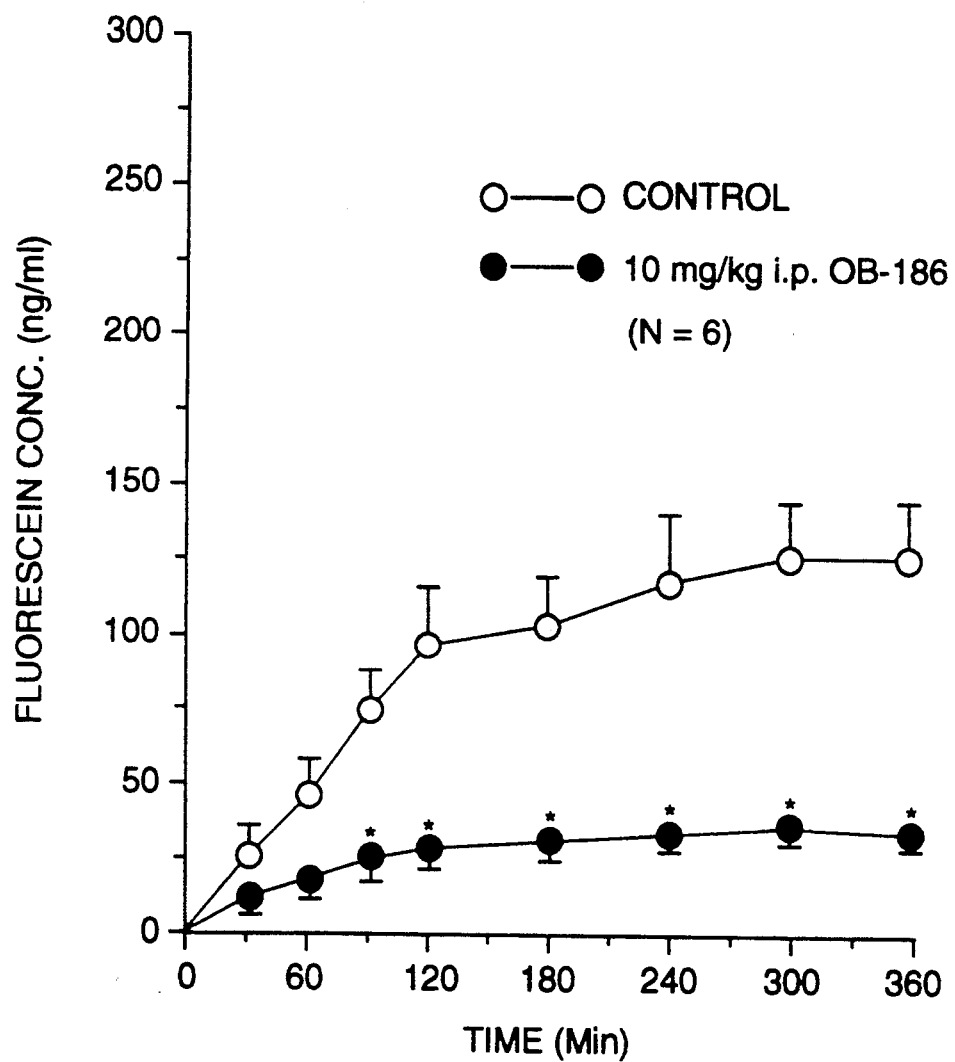
FIG. 5 shows a comparison of the effects of 10 mg/kg OB-186 tid delivered intraperitoneally on intravitreally injected endotoxin-induced uveitis to that of a control that received no drug. Each point is a mean of 6 values for fluorescein concentration in the posterior part of the eye. The bars represent SEM and the asterisks indicate the significant difference from the corresponding control values at $p<0.05$.

In the case of 10 mg/kg OB-186 tid, all uveitis responses measured at 1, 2, 3, 4, 5, and 6 hours after fluorescein injection were suppressed significantly (FIG. 5). During the experiments, no obvious side effects were noted as a result of the treatment of the animals with OB-186.

Figure 6:
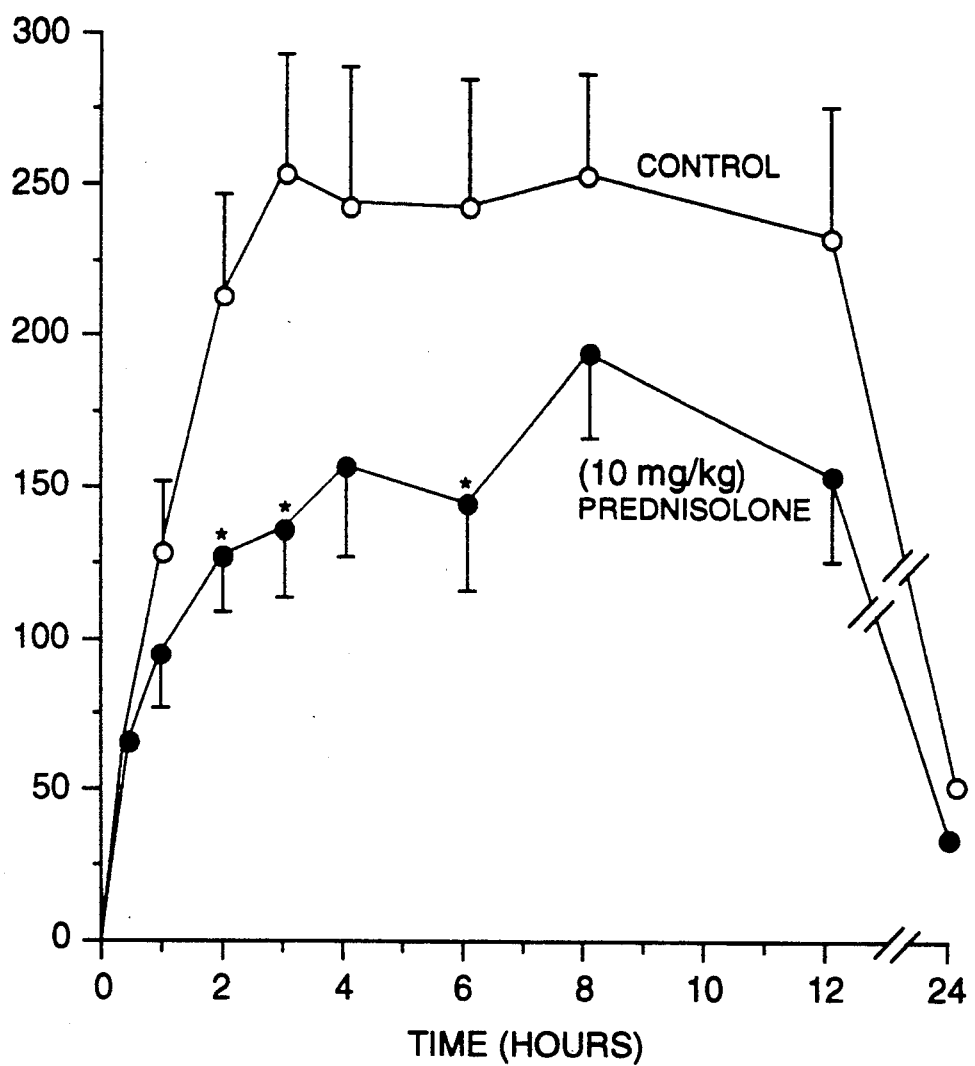
FIG. 6 shows a comparison of the effects of 10 mg/kg prednisolone tid delivered intraperitoneally on intravitreally injected endotoxin-induced uveitis to that of a control that received no drug. Each point is a mean of eight values for fluorescein concentration in the posterior part of the eye. The bars represent SEM and the asterisks indicate the significant difference from the corresponding control values at $p<0.05$.

FIG. 6 shows the inhibition of endotoxin induced uveitis by i mg/kg prednisolone tid. Uveitis responses measured at 2, 3, and 6 hours after fluorescein were suppressed significantly at an average inhibition of 42%. These results indicate that prednisolone is less potent than OB-186 to inhibit the posterior uveitis.

What is claimed is:

1. A method for controlling ocular inflammation which method comprises administering an inflammation-controlling effective amount of a pharmaceutical composition comprising a pharmaceutically acceptable vehicle in admixture with a compound having the formula:

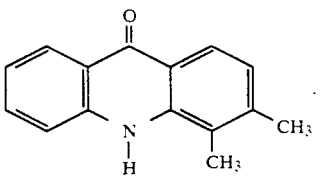

2. The method of claim 1 wherein the ocular inflammation is posterior uveitis.
3. The method of claim 1 wherein the ocular inflammation is in the anterior portion of the eye.
4. The method of claim 1 wherein the compound is administered orally.
5. The method of claim 1 wherein the compound is administered parenterally.
6. The method of claim 1 wherein the compound is administered topically.
7. The method of claim 2 wherein the compound is injected parenterally.
8. The method of claim 3 wherein the compound is administered topically.
9. A method for controlling ocular inflammation which method comprises inserting an ocular delivery device into the eye, said ocular delivery device comprising an inflammation-controlling effective amount of a compound having the formula:

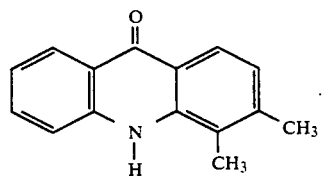

10. A method for controlling of systemic inflammatory disease which method comprises administering an effective amount of a compound having the formula:

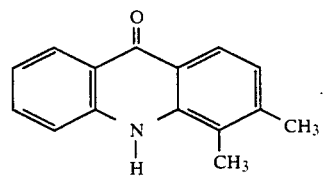

11. The method according to claim 10 wherein said disease in rheumatoid arthritis, inflammatory bowel disease, glomerulonephritis, allergic inflammation or allergic encephalomyelitis.
12. A pharmaceutical composition useful for controlling ocular inflammation or systemic inflammatory disease comprising an effective amount of a compound having the formula:

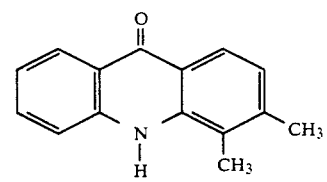

in admixture with a pharmaceutically acceptable vehicle.

* * * * *